United States Patent [19]

Hsu et al.

[11] 4,365,079
[45] Dec. 21, 1982

[54] RECOVERY OF DIMETHYL SEBACATE FROM AN ISOMERIC MIXTURE OF $C_{12}$ ESTERS

[75] Inventors: Chao-Yang Hsu, Media; Haven S. Kesling, Jr., Drexel Hill, both of Pa.

[73] Assignee: Atlantic Richfield Company, Los Angeles, Calif.

[21] Appl. No.: 222,477

[22] Filed: Jan. 5, 1981

[51] Int. Cl.$^3$ ............... C07C 67/52; C07C 67/303
[52] U.S. Cl. ........................... 560/191; 560/190
[58] Field of Search .......................... 560/190, 191

[56] References Cited
U.S. PATENT DOCUMENTS 2,824,123  2/1958  Kuceski ........................... 560/191

Primary Examiner—Natalie Trousof
Assistant Examiner—Vera C. Clarke
Attorney, Agent, or Firm—Delbert E. McCaslin

[57] ABSTRACT

Dimethyl sebacate is recovered from a reaction mixture containing it in predominant amount and minor amounts of other dimethyl esters of $C_{10}$-dicarboxylic acids by stepwise recrystallization using a solvent selected from the group consisting of acetone, diethyl ether, tetrahydrofuran, alkanols having 1 to 4 carbon atoms, aromatic hydrocarbons having 6 to 12 carbon atoms, alkanes and alkenes having 5 to 8 carbon atoms or a mixture of one of those solvents which is miscible with water, and water as recrystallization solvent.

6 Claims, No Drawings

RECOVERY OF DIMETHYL SEBACATE FROM AN ISOMERIC MIXTURE OF $C_{12}$ ESTERS

BACKGROUND OF THE INVENTION

Various processes such as fractional distillation, fractional recrystallization, solvent extraction and the urea adduct method are known for the separation of linear fatty acids or esters from other reaction by-products. Fractional distillation is limited to the separation of fatty acids or esters of different chain lengths. Because of the small differences in the boiling points, fractional distillation is impractical for the separation of acid or ester isomers with the same chain length.

Fractional recrystallization and solvent extraction methods of separation are generally used for the isolation of saturated fatty acids from unsaturated ones.

The urea adduct method has been shown to be an efficient method for the separation of straight chain aliphatic compounds from branched chain and cyclic isomers. This method can also be used for the separation of compounds of different degrees of saturation and chain length. However, due to unfavorable economics, the urea adduct method is impractical as a commercial separation process.

The present invention is based on the discovery that dimethyl sebacate may be recovered from a reaction mixture containing it in predominant amount and minor amounts of other dimethyl esters of $C_{10}$-dicarboxylic acids by stepwise recrystallization providing certain solvents are used for that purpose.

BRIEF DESCRIPTION OF THE INVENTION

A high yield of high purity dimethyl sebacate may be recovered from a reaction mixture containing the same in predominant amount together with minor amounts of other dimethyl esters of $C_{10}$-dicarboxylic acids by stepwise recrystallization of dimethyl sebacate from said reaction mixture using a solvent selected from the group consisting of acetone, diethyl ether, tetrahydrofuran, alkanols having 1 to 4 carbon atoms, aromatic hydrocarbons having 6 to 12 carbon atoms, alkanes and alkenes having 5 to 8 carbon atoms and a mixture of one of said solvents which is miscible with water, and water.

Preferably, the mixture of dimethyl esters of the $C_{10}$-dicarboxylic acids from which dimethyl sebacate is recovered is produced by the steps of contacting methyl penta-2,4-dienoate in a reaction inert solvent at a temperature of 30° to 150° C. under an inert atmosphere with a catalytic amount of a homogeneous palladium (II) complex catalyst, hydrogenating resulting reaction mixture, removing unreacted methyl penta-2,4-dienoate and reaction inert solvent by fractional distillation at reduced pressure, separating the ester of the $C_{15}$-tricarboxylic acid (trimer) and other minor heavy by-products by distilling off the esters of the $C_{10}$-dicarboxylic acids including dimethyl sebacate and recovering resulting mixture of the esters of the $C_{10}$-dicarboxylic acids.

DETAILED DESCRIPTION OF THE INVENTION

Dimethyl sebacate may be produced by contacting methyl penta-2,4-dienoate, in a reaction inert medium, at a temperature of 30° to 150° C. under an inert atmosphere with a catalytic amount of a homogeneous palladium (II) complex of the formula

wherein Q is phosphorous or arsenic; R is alkyl, trichloroalkyl, tribromoalkyl or trifluoroalkyl having from 1 to 6 carbon atoms or aryl having 6 to 12 carbon atoms and R' is alkyl, aminoalkyl or alkoxy having 1 to 6 carbon atoms or aryl or aryloxy having 6 to 12 carbon atoms, and then hydrogenating resulting reaction mixture under a hydrogen pressure of from 1 to 50 atmospheres and at a temperature of from 30° to 200° C. in the presence of a catalytic amount of a hydrogenation catalyst which converts unsaturated esters to saturated esters.

Generally, a catalytic amount of said palladium (II) complex catalyst ranges from about 0.1 to 5 mole % of the starting methyl penta-2,4-dienoate. Preferably, the amount of catalyst is between 0.5 and 2 mole % of said starting material.

The palladium (II) complex catalyst is a homogeneous catalyst, i.e. it is soluble in the employed solvent medium. Typical examples of suitable solvents for the reaction inert medium in which the catalyst is insoluble are tetrahydrofuran, diethyl ether, dioxane, acetone, acetonitrile, methyl and ethyl acetate, chloroform, benzene, toluene and dimethyl sulfoxide. The catalyst may be preformed or generated in situ. In the latter case, the molar ratio of

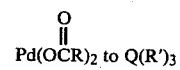

preferably ranges from 1:0.5 to 1:3.

Preferred inert atmospheres for the purpose of contacting methyl penta-2,4-dienoate with said palladium (II) complex catalyst include nitrogen and carbon dioxide at a pressure range of 15 to 750 psig.

The preferred temperature for contacting methyl penta-2,4-dienoate with said palladium (II) complex catalyst is from 50° to 100° C.

Preferably, the reaction mixture obtained by contacting methyl penta-2,4-dienoate with said homogeneous palladium (II) complex catalyst is cooled to a temperature such as 0° C. in order to isolate the catalyst. Alternatively, the mixture can be subjected to distillation so as to isolate the catalyst as a residue for possible recycle.

The aforesaid hydrogenation step is preferably carried out at a hydrogen pressure of from 1 to 10 atmospheres and at a temperature of 100° to 125° C. The types of hydrogenation catalysts which may be employed in this hydrogenation have been extensively described in the prior art and any known hydrogenation catalyst, or mixture of catalysts, useful for the conversion of unsaturated esters to saturated esters may be used. Catalysts and the preparation thereof as described in U.S. Pat. Nos. 2,094,611, 2,201,235, and 3,374,184 and British Pat. Nos. 575,380, 1,151,567 and 1,181,137 may be used. In general heterogeneous catalysts comprising finely divided platinum, palladium, rhodium, ruthenium, cobalt and nickel which may be supported may be employed. Platinum oxides and palladium oxides, Raney nickel, platinum group metals on alumina or carbon may also be employed. Hydrogenation catalysts containing copper either in elemental form or combined with oxygen, as well as other hydrogenating metal oxides employed in conjunction with copper, supported or unsupported, may be used. Homogeneous hydrogenation catalysts may also be used, for example sodium carbonate tris(triphenylphosphine)rhodium chloride as described in British Pat. No. 1,181,137, hydrido tris(triphenylphosphine)ruthenium (II) chloride, tris(triphenylphosphine)ruthenium chloride and tripyridine rhodium (III) chloride. The amount of hydrogenation catalyst ranges from about 0.1 to 5 mole % of the starting methyl penta-2,4-dienoate which is dimerized.

Following hydrogenation as described above, the reaction mixture obtained contains hydrogenated methyl penta-2,4-dienoate, reaction inert solvent, dimethyl sebacate, other dimethyl esters of $C_{10}$-dicarboxylic acids, an ester of a $C_{15}$-tricarboxylic acid and minor amounts of other heavy by-products. This reaction mixture is first preferably distilled at reduced pressure to remove hydrogenated methyl penta-2,4-dienoate and reaction inert solvent. Preferably, a temperature of $\leq 50°$ C. under 10 mm Hg is used for this step. The distilland may then be distilled under reduced pressure, e.g. $\leq 135°$ C. under 0.5 mm Hg, so as to distill off the dimethyl esters of the $C_{10}$-dicarboxylic acids including dimethyl sebacate. It is the resulting reaction mixture containing dimethyl sebacate in predominant amount and minor amounts of other dimethyl esters of $C_{10}$-dicarboxylic acids which is preferably used in the present invention.

In accordance with the present invention, stepwise recrystallization involves at least two steps, the first step being preferably performed at a temperature of 0° to 20° C. and the second step being preferably performed at a temperature of from 0° to $-15°$ C. Lower temperatures can be employed and the use thereof depends on the content of dimethyl sebacate in the mixture of dimethyl esters of the $C_{10}$-dicarboxylic acids. In general, the higher the content of dimethyl sebacate, the higher the temperature that may be employed. Moreover, the higher the purity of dimethyl sebacate desired, the greater the number of steps of stepwise recrystallization.

The following examples are for the purpose of illustrating the present invention and are not limiting to the scope thereof which is set forth in the claims.

EXAMPLE 1

Into a dry heavy wall glass reactor, there was introduced methyl penta-2,4-dienoate (25 mmole), diacetate-bis(triphenylphosphine)palladium (II) (0.5 mmole), and toluene (20 ml). The reactor was sealed, and deoxygenated with a purge of nitrogen. While stirring, the reaction mixture was heated to 40° C. for 4 hours. After cooling the reaction mixture to 25° C. and separating the palladium complex catalyst, the reaction mixture was transferred to a Parr hydrogenation bottle. Palladium on carbon catalyst (5%, 1.0 g), and tetrahydrofuran (25 ml) was added into the reaction mixture. After the reaction system was purged with hydrogen, the reaction mixture was hydrogenated under 3 atm of hydrogen pressure until no further pressure drop was observed. The resulting hydrogenated reaction products were separated from the solid catalyst by filtration. The solvents and hydrogenated methyl penta-2,4-dienoate were removed by distillation at $\leq 50°$ C. under 10 mm Hg. and then the mixture of dimethyl esters of $C_{10}$-dicarboxylic acids including dimethyl sebacate were separated from the ester of the $C_{15}$-tricarboxylic acid by distillation at $\leq 135°$ C. under 0.5 mm Hg.

EXAMPLE 2

A mixture of esters of $C_{10}$-dicarboxylic acids (24 g), obtained in accordance with the general procedure of Example 1, containing dimethyl sebacate (81.5%), branched isomer (10.3%), cyclic isomer (1.1%), and other by-products (7.1%) was mixed with 24 ml of pentane at ambient temperature. The mixture was then cooled with an ice-water bath until the temperature lowered to 0° C., at which point fine white crystals dropped out of solution. The upper liquid layer was then decanted. The crystals were then heated until a liquid was obtained, and 24 ml of pentane was added. After cooling to 0° C., white crystals again dropped out of the solution. The liquid pentane layer was decanted. The solids were then heated until completely liquefied, and the entrained pentane was stripped off by rotary evaporation. Gas chromatographic analysis of the isolated solid phase (17.7 g) revealed the following composition: dimethyl sebacate (99.0%), branched isomer (1.0%). The two decanted pentane phases were combined. After stripping off pentane, 6.3 g of dimethyl esters of $C_{10}$-dicarboxylic acids was obtained. The second recrystallization was then made by adding 6.3 ml of pentane, and the mixture was cooled to $-5°$ C. An additional crop of solid (1.4 g) was separated. Gas chromatographic analysis of this crop revealed the following composition: dimethyl sebacate (92.4%), branched isomer (5.6%), cyclic isomer (0.6%), and others 1.4%. Thus, after two simple recrystallizations in pentane solvent, a 95.9% of dimethyl sebacate was recovered with a 98.4% purity.

EXAMPLE 3

The use of methanol as a recrystallization solvent was studied employing the same procedure as described in Example 2. A dimethyl sebacate recovery of 73.4% with a 96.9% purity was obtained.

We claim:

1. A process for recovering dimethyl sebacate from a reaction mixture containing dimethyl sebacate in predominant amount and minor amounts of other dimethyl esters of $C_{10}$-dicarboxylic acids which comprises stepwise recrystallizing dimethyl sebacate from said reaction mixture using a solvent selected from the group consisting of acetone, diethyl ether, tetrahydrofuran, alkanols having 1 to 4 carbon atoms, aromatic hydrocarbons having 6 to 12 carbon atoms, alkanes and alkenes having 5 to 8 carbon atoms and a mixture of one of said solvents which is miscible with water, and water.

2. The process of claim 1 wherein the first step of recrystallization is performed at a temperature of 0° to 20° C. and the second step is performed at a temperature of from 0° to $-15°$ C.

3. The process of claim 1 wherein the amount of recrystallization solvent ranges from 25 to 500% by weight based on the weight of the dimethyl esters of $C_{10}$-dicarboxylic acids present in said reaction mixture.

4. In the process of producing dimethyl sebacate by contacting, in a reaction inert solvent, methyl penta-2,4-dienoate at a temperature of 30° to 150° C. under an inert atmosphere with a catalytic amount of a homogeneous palladium (II) complex of the formula

wherein Q is phosphorous or arsenic; R is alkyl, trichloroalkyl, tribromoalkyl or trifluoroalkyl having from 1 to 6 carbon atoms or aryl having 6 to 12 carbon atoms and R' is alkyl, aminoalkyl or alkoxy having 1 to 6 carbon atoms or aryl or aryloxy having 6 to 12 carbon atoms and hydrogenating resulting reaction mixture at a hydrogen pressure of from 1 to 50 atmospheres and at a temperature of from 30° to 100° C. in the presence of a catalytic amount of a hydrogenation catalyst which converts unsaturated ester to saturated ester, the improved method of recovering dimethyl sebacate from said reaction mixture containing hydrogenated methyl penta-2,4-dienoate, reaction inert solvent, dimethyl sebacate, other dimethyl esters of $C_{10}$-dicarboxylic acids, an ester of a $C_{15}$-tricarboxylic acid and other minor heavy by-products which comprises removing hydrogenated methyl penta-2,4-dienoate and reaction inert solvent by fractional distillation at reduced pressure, separating the ester of the $C_{15}$-tricarboxylic acid and other minor heavy by-products by distilling off the dimethyl ester of the $C_{10}$-dicarboxylic acids including dimethyl sebacate at reduced pressure and stepwise recrystallizing dimethyl sebacate from resulting mixture of the esters of the $C_{10}$-dicarboxylic acids using a solvent selected from the group consisting of acetone, diethyl ether, tetrahydrofuran, alkanols having 1 to 4 carbon atoms, aromatic hydrocarbons having 6 to 12 carbon atoms, alkanes and alkenes having 5 to 8 carbon atoms and a mixture of one of said solvents which is miscible with water, and water.

5. The process of claim 4 wherein the first step of recrystallization is performed at a temperature of 0° to 20° C. and the second step is performed at a temperature of from 0° to −15° C.

6. The process of claim 4 wherein the amount of recrystallization solvent ranges from 25 to 500% by weight based on the weight of the mixture of esters of $C_{10}$-dicarboxylic acids including dimethyl sebacate.

* * * * *